United States Patent
Bedekar et al.

(10) Patent No.: US 6,838,582 B2
(45) Date of Patent: Jan. 4, 2005

(54) PROCESS FOR PREPARING 2,4,4,6-TETRABROMO-2,5-CYCLOYHEXADIENONE

(75) Inventors: Ashutosh Vasant Bedekar, Gujarat (IN); Ramachandraiah Gadde, Gujarat (IN); Pushhpito Ghosh, Gujarat (IN)

(73) Assignee: Council of Scientific and Industrial Research, New Delhi (IN)

( * ) Notice: Subject to any disclaimer, the term of this patent is extended or adjusted under 35 U.S.C. 154(b) by 14 days.

(21) Appl. No.: 10/335,124

(22) Filed: Dec. 31, 2002

(65) Prior Publication Data

US 2004/0127750 A1 Jul. 1, 2004

(51) Int. Cl.[7] .......................... C07C 45/29; C07C 45/30
(52) U.S. Cl. ...................................... 568/361; 568/364
(58) Field of Search ................................ 568/361, 364

(56) References Cited

U.S. PATENT DOCUMENTS 4,250,341 A * 2/1981 Needham et al. ........... 568/361
4,954,662 A * 9/1990 Desmurs et al. ............ 568/779
6,365,786 B1   4/2002 Ramachandraiah et al.

OTHER PUBLICATIONS

L Chas Raiford et al., "Some bromination products of the fluorophenols" Journal of the American Chemical Society, vol. 66, 1944, pp. 2080–2082, XP 002252362, American Chemical Society, Washington, DC, pp. 2080–2082.

* cited by examiner

Primary Examiner—Johann Richter
Assistant Examiner—Sikarl A. Witherspoon
(74) Attorney, Agent, or Firm—Darby & Darby

(57) ABSTRACT

A highly pure 2,4,4,6-tetrabromo-2,5-cyclohexadienone has been prepared in a single pot, eco-friendly procedure in yields of 91–94% from phenol. In this method, a mixture of alkali/alkaline earth metal bromide and alkali/alkaline earth metal bromate was employed as brominating agent in place of corrosive liquid bromine. The reaction between phenol and the brominating reagent was initiated by the action of a mineral acid or moderately strong organic acid. The crude product was further characterized by standard analytical and spectroscopic methods.

15 Claims, No Drawings

PROCESS FOR PREPARING 2,4,4,6-TETRABROMO-2,5-CYCLOYHEXADIENONE

FIELD OF THE INVENTION

The present invention relates to a process for the single pot preparation of 2,4,4,6-tetrabromo-2,5-cyclohexadienone.

BACKGROUND OF THE INVENTION 2,4,4,6-Tetrabromo-2,5-cyclohexadienone has wide applications in synthetic organic chemistry. It is used in preparation of linear poly(phenyleneoxides) (W. Ried et al. Angew. Chem., Int. Ed. Engl. 8, 379, 1969), direct monobromination of imidazoles and N-methylindoles (V. Calo et al. J. Chem. Soc., Perkin Trans.-1, 2567, 1972); in regioselective monobromination of aromatic amines to form 4-bromoanilines in high yields (V. Calo et al. J. Chem. Soc. C, 3652, 1971); para bromination of phenols by regioselective bromination of phenols (V. Calo et al. Chem. Ind. (Milan), 53, 467, 1971); for bromination of thiophenes (C. Slemon U.S. Pat. No. 5,371,240; CA 1995, 122, 132966); for preparation of $\alpha,\mu$-unsaturated bromoketones. (V. Calo at el. Tetrahedron 29, 1625, 1973); for ring expansion reaction (M. Lanz et al. Helv. Chim. Acta 80, 804, 1997); for preparation of brominated algal components via bromination of myrcene. (T. Yoshihara et al. Bull. Chem. Soc. Jpn. 51, 653, 1978); for direct brominative ring closure. (T. Kato et al. Bioorg. Chem. 4, 188, 1975); for synthesis of carbocyclic molecules (I. Ichinose et al. Chem. Lett. 61, 1979); preparation of brominated polyenes and brominated dihydroionylideneacetates (Jpn. Kokai Tokkyo Koho 78,112, 852; CA 1979, 90, 87701); in stereocontrolled synthesis of disubstituted tetrahydrofurans (P. C. Ting et al. J. Am. Chem. Soc. 106, 2668, 1984); for oxidative synthesis of disulphides (T. L. Ho et al. Synthesis 872, 1974); in intramolecular cyclisation of phenolic oximes as a key step in synthesis of cis,cis-aerothionin (A. R. Forrestewr et al. Justus Liebigs Ann. Chem. 66, 1978); in synthesis of 6-bromocamphene and 9-bromolongifolene (T. Onishi et al. Jpn. Kokai Tokkyo Koho JP 60,181,037; CA 1986, 104, 110003); as reagent combination for converting alcohols to azides (A. Tanaka et al. Tetrahedron Lett. 38. 3955, 1997), silylethers to alkylbromides (A. Tanaka et al. Tetrahedron Lett. 38, 7223, 1997) and tetrahydropyranylethers to alkylbromides (A. Tanaka et al. Tetrahedron Lett. 38, 1955, 1997); in several total syntheses (B. M. Trost et al. J. Am. Chem. Soc. 105, 5075, 1983; T. Kato et al. J. Chem. Soc., Chem. Commun. 1077, 1984; F. E. Ziegler et al. J. Am. Chem. Soc. 112, 2749, 1990; K. Tatsuta et al. Bull. Chem. Soc. Jpn. 70, 427, 1997; K. Tatsuta et al. Pure Appl. Chem., 68, 1341, 1996; N. D. Pearson et al. Tetrahedron Lett., 35, 3771, 1994; G. Mehta et al. J. Chem. Soc., Chem. Commun. 1319, 1986; D. Yang et al. J. Am. Chem. Soc. 120, 5943, 1998; I. C. Gonzalez et al. J. Am. Chem. Soc. 122, 9099, 2000); for allylic bromination of $\mu$-lactam antibiotics (Jpn. Kokai Tokkyo Koho JP 59 88,489; CA 1984, 101, 170973) and as sensitizer for photooxygenation of dioxenes. (L. Lopez et al. J. Chem. Soc., Chem. Commun. 1266, 1984, and Photochem. 32, 95, 1986).

Reference is made to M. Tsubota et al. (Bull. Chem. Soc. Jpn. 45, 1252, 1972) wherein the bromination of 2,4,6-tribromophenol was carried out by employing liquid bromine. In this process, 50 mmol (8 g) of bromine was added to 37.2 mmol (12.3 g) of 2,4,6-tribromophenol at 2–3° C. in 1:1 (v/v) methanol-acetic acid. The yellow precipitate of the desired product was obtained by adding 50 ml of 10% aqueous sodium carbonate solution to the reaction mixture. The yield of the uncrystalized product with a melting point of 136° C. was 90% (15 g, 36.5 mmol).

The drawbacks of this procedure are that it requires the handling of hazardous liquid bromine and the reaction. The process requires neutralization step to neutralize the acetic acid with sodium carbonate after the completion of the reaction. Additional steps are required to recover the methanol and the sodium acetate from the effluent for its safe discharge and to make the process more economically viable and thus the process is costly. Moreover, the reaction has to be conducted at low temperature which requires special cooling devices that affect the cost of production. Moreover, this method starts tribromophenol, an already brominated phenol as raw material. Further, the process liberates hydrobromic acid as byproduct which requires sodium carbonate to neutralize along with the acetic acid. The total bromine ended up in the reaction would be not more than 50%. Besides, the yield is only 90%.

V. Calo et al. (J. Chem. Soc. C. 3652 1971) and G. J. Fox et al. (Org. Synth. Coll. Vol. VI 181, 1988) have stated a method of bromination of 2,4,6-tribromophenol employing liquid bromine. In this process, bromine and 2,4,6-tribromophenol were reacted in equimolar ratio in sodium acetate and acetic acid mixture at room temperature. The reaction mixture was poured into crushed ice to get yellow precipitates of 2,4,4,6-tetrebromo-2,5-cyclohexadienone. The crude product was dissolved in warm chloroform and allowed to crystallize on cooling to yield 61–67% of product having a melting point in the range of 125–130° C.

The drawbacks of this procedure are that it still possesses the handling of hazardous liquid bromine and requires special equipment. Moreover, 50% of the liquid bromine ends up in the effluent in the form hydrobromic acid. The effluent is hazardous as it contains sodium acetate, acetic acid and hydrobromic acid which require additional steps such as neutralization and separation for safe discharge costing production heavily.

OBJECTS OF THE INVENTION

The main object of the invention is to provide an improved process for the single pot synthesis of 2,4,4,6-tetrabromo-2,5-cyclohexadienone which obviates the above drawbacks.

Another object of the invention is to obtain 2,4,4,6-tetrabromo-2,5-cyclohexadienone by the direct bromination of phenol.

Still another object of the invention is to use the combination of alkali metal/alkaline earth metal bromides and alkali metal/alkaline earth metal bromates as brominating reagent.

Yet another object of the invention is to use mineral acids or moderately strong organic acids as one of the reactants.

Yet another object of the invention is to prepare 2,4,4,6-tetrabromo-2,5-cyclohexadienone at ambient temperature.

Yet another object of the invention is to maximize bromine atom utilization in the reaction.

Yet another object of the invention is to minimize pollutants in the generated wastes.

SUMMARY OF THE INVENTION

Accordingly the present invention provides a process for the single pot preparation of 2,4,4,6-tetrabromo-2,5-cyclohexadienone by reacting phenol with a brominating agent comprising a mixture of alkali/alkaline earth metal bromide and alkali/alkaline earth metal bromate dissolved in deionized water, in the presence of an acid, separating, washing and drying the precipitate to obtain 2,4,4,6-tetrabromo-2,5-cyclohexadienone.

In another embodiment of the invention, the organic acid is selected from the group comprising of oxalic acid and citric acid.

In one embodiment of the invention, the acid comprises hydrochloric acid.

In another embodiment of the invention, the phenol used is laboratory grade phenol.

In another embodiment of the invention, the process comprises reacting 2 to 10 g (21 to 106 mmoles) of phenol with a mixture of 54 to 301 mmoles of alkali/alkaline earth metal bromide and 27 to 150 mmoles of alkali/alkaline earth metal bromate dissolved in 30 (w/w) equivalents of deionized water by slowly adding 3.5 to 16.0 g (96 to 438 mmoles) of 36% hydrochloric acid in 5 (w/w) equivalents of deionized water over two hours, allowing the reaction to continue, filtering the precipitate, washing and drying under vacuum to obtain 2,4,4,6tetrabromo-2,5-cyclohexadienone.

In another embodiment of the invention the process comprises slowly adding of a solution of 54 to 301 mmoles of alkali/alkaline earth metal bromide and 27 to 150 mmoles of alkali/alkaline earth metal bromate dissolved in 15 (w/w) equivalents of deionized water to a mixture of 2 to 10 g (21 to 106 mmoles) of phenol and 3.5 to 16.0 g (96 to 438 mmoles) 36% hydrochloric acid in 20 (w/w) equivalents of deionized water over two hours; continuing the stirring for two hours, filtering the precipitate, washing and drying to obtain 2,4,4,6-tetrabromo-2,5-cyclohexadienone.

In yet another embodiment of the invention the process comprises the instantaneous addition of 87 to 436 mmoles of a moderately strong organic acid dissolved in 5 (w/w) equivalents of water to a mixture of phenol, an alkali/alkaline earth metal bromide and an alkali/alkaline earth metal bromate in 30 (w/w) equivalents of water; allowing the mixture to react for 8–10 hours under stirring at 27 to 35° C., filtering, washing with deionized water and drying the precipitate under vacuum to obtain 2,4,4,6-tetrabromo-2,5-cyclohexadienone.

In one embodiment of the invention, the brominating agent comprises a combination of for every 54 to 301 mmoles of alkali/alkaline earth metal bromides, 27 to 150 mmoles of alkali/alkaline earth metal bromates.

In yet another embodiment of the invention, the bromination of phenol is initiated by adding 36% hydrochloric acid in 10 to 50 ml of water and a brominating agent comprising alkali/alkaline earth metal bromide and alkali/alkaline earth metal bromate dissolved in 60 to 300 ml of water.

In yet another embodiment of the invention, the bromination reaction is conducted at a temperature in the range of 27–35° C.

In yet another embodiment of the invention, the bromination of phenol is initiated by adding a mixture of alkali/alkaline earth metal bromide and alkali/alkaline earth metal bromate dissolved in 60 to 300 ml of water to a mixture of phenol and 36% hydrochloric acid in 10 to 50 ml of water.

In another embodiment of the invention, bromination reaction is initiated by instantaneous addition of oxalic acid or citric acid dissolved in 10 to 30 ml of water to the mixture of phenol, alkali/alkaline earth metal bromide and alkali/alkaline earth metal bromate in 60 to 300 ml of water.

DETAILED DESCRIPTION OF THE INVENTION

According to the present invention, 2,4,4,6-tetrabromo-2,5-cyclohexadienone, TBCO is obtained via the overall reaction depicted in equation below.

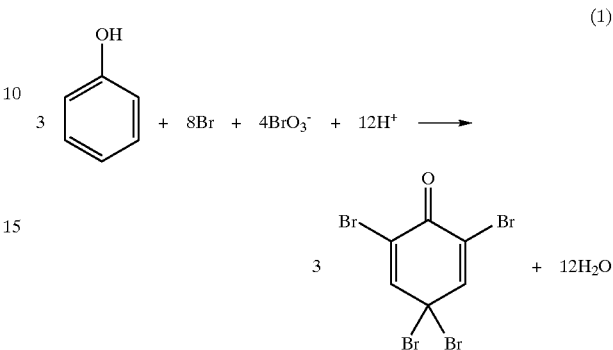

The reaction was carried out in a round bottom (0.1 or 1.0 L) flask provided with the facility to add solutions slowly from outside and a mechanical device to stir the contents in it. A known quantity of phenol and calculated amounts of laboratory grade (about 99% pure) alkali/alkaline earth metal bromide and bromate were dissolved in water. Flask temperature was maintained in the range of 27–35° C. Calculated amount of aqueous 36% hydrochloric acid was added over 2 h under stirring. Stirring was continued for an additional 2 h. The contents were filtered, crude product was washed with sufficient water, dried under vacuum, weighed and melting point determined.

In a related procedure, the required quantity of 36% hydrochloric acid was taken along with phenol dissolved in water and bromination reaction was initiated by gradual addition of an aqueous solution containing required quantities of bromide and bromate salts.

In another related procedure, the required quantities of the salts of bromide and bromate and the organic acid in minimum quantity of water were taken along with the phenol and the intended reaction was allowed with time under constant stirring. The temperature of the vessel was observed between 27–35° C. The use of hydrochloric acid is advisable as it minimizes the reaction time. The reaction product was characterized through elemental analysis, $^1$H-NMR, IR and melting point.

The present invention describes a single pot preparation of 2,4,4,6-tetrabromo-2,5-cyclohexadienone by bromination of phenol employing a mixture of alkali/alkaline earth metal bromides and bromates and a mineral or organic acid.

The process of the invention involves i) reaction of phenol with a mixture of alkali/alkaline earth metal bromide and alkali/alkaline earth metal bromate in deionized water by slow addition of 36% hydrochloric acid over a period of two hours; (ii) alternatively, slow addition of aqueous solution of alkali/alkaline earth metal bromide and alkali/alkaline earth metal bromate to a mixture of phenol and 36% hydrochloric acid over a period of two hours and stirring for another two hours., or optionally; (iii) the instantaneous addition of a moderately strong organic acid to aqueous solution of phenol, alkali/alkaline earth metal bromide and alkali/alkaline earth metal bromate and stirring for 8–10 hours at ambient temperature. The resulting product was separated by filtration, washed with deionized water and dried under vacuum to yield 91 to 94% of crude 2,4,4,6-tetrabromo-2,5-cyclohexadienone melting at 123 to 127° C.

The inventive steps involved in the present invention are
i) alkali/alkaline earth metal bromides, alkali/alkaline earth metal bromates are used to generate reactive bromine species, which dispenses the need of liquid bromine,
ii) starting material for this synthesis is readily and cheaply available phenol, compared to 2,4,6-tribromophenol,
iii) reaction is carried out in purely aqueous medium, eliminating the need to use organic solvents which needs one more unit operation to recover organic solvent.

The following examples are given by way of illustration and should not be construed to limit the scope of the present invention.

EXAMPLE—1

To a well stirred solution of 2.00 g (21 mmoles) of phenol, 5.97 g (58 mmoles) of sodium bromide and 4.38 g (29 mmoles) of sodium bromate in 60 ml deionized water, in a two neck 100 ml round bottom flask, was slowly added 8.7 mL (3.14 g; 86 mmoles) of 36% hydrochloric acid over 2 h. The contents were stirred for another 2 h. The precipitated product was filtered, washed twice with deionized water and dried in vacuum for 6 h. The total crude yield of 2,4,4,6-tetrabromo-2,5-cyclohexadienone was 8.11 g (93%). The characteristic data recorded for the isolated sample with melting point 125° C.: IR (KBr) υ 634, 663, 702, 900, 1310, 1454, 1582, 1680, 3051 cm$^{-1}$; $^1$H-NMR (CDCl$_3$, 200 MHz) δ 7.78 (s, 2H) and elemental analysis, observed 17.16 (% C); 0.24 (% H), calculated for C$_6$H$_2$Br$_4$O; 17.56 (% C); 0.49 (% H).

EXAMPLE—2

To a well stirred solution of 10.00 g (106 mmoles) of phenol, 29.60 g (287 mmoles) of sodium bromide and 21.70 g (144 mmoles) of sodium bromate in 275 ml deionized water in a two neck 500 ml round bottom flask, a mixture of 43.7 mL (15.70 g; 431 mmoles) of 36% hydrochloric acid in 50 mL water was slowly added over 2 h. The contents were stirred for another 2 h. The precipitated product was filtered, washed twice with deionized water and dried in vacuum for 6 h. Total crude yield of 2,4,4,6-tetrabromo-2,5-cyclohexadienone was 40.1 g (92%). The characteristic data recorded for the isolated sample with melting point, 125° C.; IR (KBr) υ 634, 663, 702, 900, 1310, 1454, 1582, 1680, 3051 cm$^{-1}$; $^1$H-NMR (CDCl$_3$, 200 MHz) δ 7.78 (s, 2H) and elemental analysis, observed 17.16 (% C); 0.24 (% H), calculated for C$_6$H$_2$Br$_4$O; 17.56 (% C); 0.49 (% H).

EXAMPLE—3

To a solution of 5.00 g (53 mmoles) of phenol and 22.0 mL (7.93 g; 220 mmoles) of 36% hydrochloric acid in 100 mL deionized water in 500 mL two neck flask with good stirring arrangement was slowly added a mixture of 15.00 g (145 mmoles) of sodium bromide and 10.93 g (72 mmoles) of sodium bromate in 50 ml deionized water over 2 h. After additional stirring (2 h) the precipitated product was separated by filtration, washed with deionized water and dried under vacuum to afford 19.8 g (91%) of crude 2,4,4,6-tetrabromo-2,5-cyclohexadienone melting at 125 degree C.; IR (KBr) υ 634, 663, 702, 900, 1310, 1454, 1582, 1680, 3051 cm$^{-1}$; $^1$H-NMR (CDCl$_3$, 200 MHz) δ 7.78 (s, 2H) and elemental analysis, observed 17.16 (% C); 0.24 (% H), calculated for C$_6$H$_2$Br$_4$O; 17.56 (% C); 0.49 (% H).

EXAMPLE—4

To a well stirred solution of 5.00 g (53 mmoles) of phenol, 15.00 g (145 mmoles) of sodium bromide and 10.93 g (72 mmoles) of sodium bromate in 100 mL of deionized water in a 250 ml round bottom flask, was slowly added a solution of 27.72 g (220 mmoles) of oxalic acid dihydrate in 50 mL water over 10 min. The contents were stirred for another 8 h. The precipitated product was filtered, washed twice with deionized water and dried in vacuum for 6 h. The total crude yield of 2,4,4,6-tetrabromo-2,5-cyclohexadienone was 20.5 g (94%) which melted at 123 degree C.; IR (KBr) υ 634, 663, 702, 900, 1310, 1454, 1582, 1680, 3051 cm$^{-1}$; $^1$H-NMR (CDCl$_3$, 200 MHz) δ 7.78 (s, 2H) and elemental analysis, observed 17.16 (% C); 0.24 (% H), calculated for C$_6$H$_2$Br$_4$O; 17.56 (% C); 0.49 (% H).

The Main Advantages of this Method are
1. It does not use directly liquid bromine for bromination of phenol.
2. It does not require to start the reaction with tribromophenol.
3. The brominating agents and other reactants are eco-friendly but not toxic and air pollutants.
4. The brominating agents do not require special equipment and safety devices.
5. Toxic side products like hydrobromic acid are not produced.
6. The alkaline solution obtained as the intermediate in the process of bromine extraction from bittern by cold process can be used as brominating agent.
7. The mineral acid or the organic acid, are not hazardous and its quantity can be minimized.
8. The bromination reaction directly offers nearly pure product in solid form thereby minimizing the requirement for work-protocol and purification.
9. The process use water as the cheap and eco-friendly solvent.

We claim:

1. A process for the single pot preparation of 2,4,4,6-tetrabromo-2,5-cyclohexadienone comprising reacting phenol with a brominating agent comprising a mixture of alkali/alkaline earth metal bromide and alkali/alkaline earth metal bromate dissolved in deionized water, in the presence of an acid, separating, washing and drying the precipitate to obtain 2,4,4,6-tetrabromo-2,5-cyclohexadienone.

2. A process as claimed in claim 1 wherein the acid is selected from the group comprising of oxalic acid and citric acid.

3. A process as claimed in claim 1 wherein the acid comprises hydrochloric acid.

4. A process as claimed in claim 1 wherein the phenol used is laboratory grade phenol.

5. A process as claimed in claim 1 wherein the process comprises reacting 2 to 10 g (21 to 106 mmoles) of phenol with a mixture of 54 to 301 mmoles of alkali/alkaline earth metal bromide and 27 to 150 mmoles of alkali/alkaline earth metal bromate dissolved in 30 (w/w) equivalents of deionized water by slowly adding 3.5 to 16.0 g (96 to 438 mmoles) of 36% hydrochloric acid in 5 (w/w) equivalents of deionized water over two hours, allowing the reaction to continue, filtering the precipitate, washing and drying under vacuum to obtain 2,4,4,6tetrabromo-2,5-cyclohexadienone.

6. A process as claimed in claim 1 wherein the process comprises slowly adding of a solution of 54 to 301 mmoles of alkali/alkaline earth metal bromide and 27 to 150 mmoles of alkali/alkaline earth metal bromate dissolved in 15 (w/w) equivalents of deionized water to a mixture of 2 to 10 g (21 to 106 mmoles) of phenol and 3.5 to 16.0 g (96 to 438 mmoles) 36% hydrochloric acid in 20 (w/w) equivalents of deionized water over two hours; continuing the stirring for two hours, filtering the precipitate, washing and drying to obtain 2,4,4.6-tetrabromo-2,5-cyclohexadienone.

7. A process as claimed in claim 1 wherein the process comprises the instantaneous addition of 87 to 436 mmoles of a moderately strong organic acid dissolved in 5 (w/w) equivalents of water to a mixture of phenol, an alkali/alkaline earth metal bromide and an alkali/alkaline earth metal bromate in 30 (w/w) equivalents of water; allowing the mixture to react for 8–10 hours under stirring at 27 to 35° C., filtering, washing with deionized water and drying the precipitate under vacuum to obtain 2,4,4,6-tetrabromo-2,5-cyclohexadienone.

8. A process as claimed in claim 1 wherein the brominating agent comprises a combination of for every 54 to 301 mmoles of alkali/alkaline earth metal bromides, 27 to 150 mmoles of alkali/alkaline earth metal bromates.

9. A process as claimed in claim 1 wherein the bromination of phenol is initiated by adding 36% hydrochloric acid in 10 to 50 ml of water and a brominating agent comprising alkali/alkaline earth metal bromide and alkali/alkaline earth metal bromate dissolved in 60 to 300 ml of water.

10. A process as claimed in claim 1 wherein the bromination reaction is conducted at a temperature in the range of 27–35° C.

11. A process as claimed in claim 1 wherein the bromination of phenol is initiated by adding a mixture of alkali/alkaline earth metal bromide and alkali/alkaline earth metal bromate dissolved in 60 to 300 ml of water to a mixture of phenol and 36% hydrochloric acid in 10 to 50 ml of water.

12. A process as claimed in claim 1 wherein the bromination reaction is initiated by instantaneous addition of oxalic acid or citric acid dissolved in 10 to 30 ml of water to the mixture of phenol, alkali/alkaline earth metal bromide and alkali/alkaline earth metal bromate in 60 to 300 ml of water.

13. A process for the single pot preparation of 2,4,4,6-tetrabromo-2,5-cyclohexadienone comprising reacting 2 to 10 g (21 to 106 mmoles) of phenol with a mixture of 54 to 301 mmoles of alkali/alkaline earth metal bromide and 27 to 150 mmoles of alkali/alkaline earth metal bromate dissolved in 30 (w/w) equivalents of deionized water by slowly adding 3.5 to 16.0 g (96 to 438 mmoles) of 36% hydrochloric acid in 5 (w/w) equivalents of deionized water over two hours, allowing the reaction to continue, filtering the precipitate, washing and drying under vacuum to obtain 2,4,4,6-tetrabromo-2,5-cyclohexadienone.

14. A process for the single pot preparation of 2,4,4,6-tetrabromo-2,5-cyclohexadienone comprising slowly adding of a solution of 54 to 301 mmoles of alkali/alkaline earth metal bromide and 27 to 150 mmoles of alkali/alkaline earth metal bromate dissolved in 15 (w/w) equivalents of deionized water to a mixture of 2 to 10 g (21 to 106 mmoles) of phenol and 3.5 to 16.0 g (96 to 438 mmoles) 36% hydrochloric acid in 20 (w/w) equivalents of deionized water over two hours; continuing the stirring for two hours, filtering the precipitate, washing and drying to obtain 2,4,4,6-tetrabromo-2,5-cyclohexadienone.

15. A process for the single pot preparation of 2,4,4,6-tetrabromo-2,5-cyclohexadienone comprising the instantaneous addition of 87 to 436 mmoles of a moderately strong organic acid dissolved in 5 (w/w) equivalents of water to a mixture of phenol, an alkali/alkaline earth metal bromide and an alkali/alkaline earth metal bromate in 30 (w/w) equivalents of water; allowing the mixture to react for 8–10 hours under stirring at 27 to 35° C., filtering, washing with deionized water and drying the precipitate under vacuum to obtain 2,4,4,6-tetrabromo-2,5-cyclohexadienone.

* * * * *